United States Patent
Roehrlein et al.

(10) Patent No.: US 10,195,444 B2
(45) Date of Patent: Feb. 5, 2019

(54) IMPLANTABLE HEARING ASSISTANCE APPARATUS AND CORRESPONDING SYSTEMS AND METHODS

(71) Applicant: Advanced Bionics AG, Staefa (CH)

(72) Inventors: Gerhard Roehrlein, Staefa (CH); Stefan Launer, Zurich (CH); Lee F. Hartley, Valencia, CA (US); Lakshmi Mishra, Carlsbad, CA (US); Abhijit Kulkarni, Newbury Park, CA (US); Logan P. Palmer, Santa Monica, CA (US); Mark Downing, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/125,152

(22) PCT Filed: Mar. 22, 2014

(86) PCT No.: PCT/US2014/031528
§ 371 (c)(1),
(2) Date: Sep. 10, 2016

(87) PCT Pub. No.: WO2015/147773
PCT Pub. Date: Oct. 1, 2015

(65) Prior Publication Data
US 2016/0375243 A1    Dec. 29, 2016

(51) Int. Cl.
| *A61N 1/00* | (2006.01) |
| *A61N 1/372* | (2006.01) |
| *A61N 1/378* | (2006.01) |
| *H04R 25/00* | (2006.01) |
| *A61N 1/05* | (2006.01) |
| *A61N 1/36* | (2006.01) |

(52) U.S. Cl.
CPC ....... *A61N 1/37229* (2013.01); *A61N 1/0541* (2013.01); *A61N 1/36036* (2017.08); *A61N 1/3787* (2013.01); *H04R 25/554* (2013.01); *H04R 25/602* (2013.01); *H04R 2225/021* (2013.01); *H04R 2225/31* (2013.01); *H04R 2225/67* (2013.01)

(58) Field of Classification Search
CPC .............. A61N 1/0541; A61N 1/36036; A61N 1/36038; A61N 1/37229; A61N 1/3787; A61N 1/3785; H04R 25/554; H04R 25/602; H01R 2225/021
See application file for complete search history.

(56) References Cited

U.S. PATENT DOCUMENTS

| 4,918,745 A | 4/1990 | Hitchison |
| 5,751,820 A | 5/1998 | Taenzer et al. |

(Continued)

FOREIGN PATENT DOCUMENTS

| WO | WO2013008057 | 1/2013 |
| WO | WO2013116161 | 8/2013 |

(Continued)

OTHER PUBLICATIONS

PCT International Search and Written Opinion dated Jul. 16, 2014 for PCT App. Ser. No. PCT/US2014/031528.

*Primary Examiner* — Mallika D Fairchild
(74) *Attorney, Agent, or Firm* — Henricks Slavin LLP

(57) ABSTRACT

Hearing assistance apparatus, systems and methods that involve the use of distributed power.

10 Claims, 6 Drawing Sheets

(56) References Cited

U.S. PATENT DOCUMENTS

| | | |
|---|---|---|
| 5,824,022 A | 10/1998 | Zilberman et al. |
| 6,775,389 B2 | 8/2004 | Harrison et al. |
| 6,842,647 B1 | 1/2005 | Griffith |
| 7,003,353 B1 | 2/2006 | Parkhouse |
| 7,039,466 B1 | 5/2006 | Harrison et al. |
| 7,450,994 B1 | 11/2008 | Mishra et al. |
| 7,599,508 B1 | 10/2009 | Lynch et al. |
| 8,027,733 B1 | 9/2011 | Fridman et al. |
| 8,073,171 B2 | 12/2011 | Haenggi et al. |
| 8,270,647 B2 | 9/2012 | Crawford et al. |
| 8,515,112 B2 | 8/2013 | Crawford et al. |
| 8,811,643 B2 | 8/2014 | Crawford et al. |
| 8,983,102 B2 | 3/2015 | Crawford et al. |
| 9,392,384 B2 | 7/2016 | Crawford et al. |
| 9,968,781 B2 | 5/2018 | Roehrlein et al. |
| 2003/0171787 A1 | 9/2003 | Money et al. |
| 2004/0172102 A1 | 9/2004 | Leysieffer |
| 2005/0159791 A1 | 7/2005 | Daly et al. |
| 2005/0209657 A1 | 9/2005 | Chung et al. |
| 2006/0190059 A1 | 8/2006 | Griffith |
| 2007/0027676 A1 | 2/2007 | Chambers et al. |
| 2007/0282394 A1 | 12/2007 | Segel et al. |
| 2008/0002834 A1 | 1/2008 | Hochmair |
| 2008/0177353 A1* | 7/2008 | Hirota .................... H01L 27/13 607/57 |
| 2008/0300658 A1 | 12/2008 | Meskens |
| 2009/0216296 A1 | 8/2009 | Meskens |
| 2009/0292338 A1 | 11/2009 | Gordon et al. |
| 2010/0046778 A1 | 2/2010 | Crawford et al. |
| 2010/0198303 A1 | 8/2010 | Haller et al. |
| 2010/0280307 A1* | 11/2010 | Lineaweaver ..... A61N 1/36036 600/25 |
| 2010/0329491 A1 | 12/2010 | Johansen |
| 2012/0041515 A1 | 2/2012 | Meskens et al. |
| 2012/0109297 A1 | 5/2012 | Van den Heuvel |
| 2012/0150259 A1 | 6/2012 | Meskens |
| 2012/0316618 A1 | 12/2012 | Zierhofer et al. |
| 2013/0066398 A1 | 3/2013 | Duftner et al. |
| 2014/0025138 A1 | 1/2014 | Meskens et al. |
| 2014/0064528 A1 | 3/2014 | Flood et al. |
| 2015/0224312 A1 | 8/2015 | Platz et al. |
| 2016/0375242 A1 | 12/2016 | Roehrlein et al. |
| 2017/0028199 A1 | 2/2017 | Roehrlein et al. |

FOREIGN PATENT DOCUMENTS

| | | |
|---|---|---|
| WO | WO2014003777 | 1/2014 |
| WO | WO2014035379 | 3/2014 |

* cited by examiner

FIG. 1 - Prior Art

IMPLANTABLE HEARING ASSISTANCE APPARATUS AND CORRESPONDING SYSTEMS AND METHODS

CROSS-REFERENCE TO RELATED APPLICATIONS

This application is the U.S. National Stage of PCT App. Ser. No. PCT/US2014/031528, filed Mar. 22, 2014.

BACKGROUND

1. Field

The present disclosure relates generally to hearing assistance devices such as, for example, implantable cochlear stimulation ("ICS") systems and hearing aids.

2. Description of the Related Art

A wide variety of hearing assistance devices are available. Such devices include, but are not limited to, ICS systems and hearing aids.

ICS systems are used to help the profoundly deaf perceive a sensation of sound by directly exciting the auditory nerve with controlled impulses of electrical current. Ambient sound pressure waves are picked up by an externally worn microphone and converted to electrical signals. The electrical signals, in turn, are processed by sound processor circuitry, converted to stimulation data (e.g., a pulse sequence having varying pulse widths and/or amplitudes), and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. Alternatively, the implantable electrode array may be directly inserted into the cochlear nerve without residing in the cochlea.

Referring to FIG. 1, conventional ICS systems commonly include an implantable device 11 and an external sound processor 12 with a housing 14, sound processor circuitry 16, a microphone 18 that is in communication with the sound processor circuitry, and a battery or other power supply 20. In the type of ICS system illustrated in FIG. 1, the sound processor is worn behind the ear (a "BTE sound processor") and includes an earhook 22. The sound processor 12 transmits stimulation data, as well as power from its power supply 20, to the implantable device 11 by way of an inductive link. To that end, ICS systems include a headpiece 24 that is connected to the sound processor 12 by a cable 26. The headpiece 24 has a coil antenna that is used to connect the headpiece (and BTE sound processor by way of the headpiece) to the implantable device via an inductive link. So configured, the BTE sound processor provides sound processing functionality and also provides power for the entire ICS system. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor. Other ICS systems are configured such that all of the external components (e.g., the battery, the microphone, the sound processor, and the coil) are carried within a single headpiece. One example of such a system is disclosed in U.S. Pat. Pub. No. 2010/0046778, which is entitled "Integrated Cochlear Implant Headpiece" and incorporated herein by reference in its entirety.

Hearing aids include a microphone, sound processor circuitry, and a speaker (sometimes referred to as a "receiver"). Here too, ambient sound pressure waves are picked up by the microphone and converted into electrical signals. The electrical signals, in turn, are processed by sound processor circuitry. The processed signals drive the speaker, which delivers amplified (or otherwise processed) sound pressure waves to the ear canal. Exemplary types of hearing aids include, but are not limited to, BTE hearing aids, receiver-in-canal ("RIC") hearing aids, and in-the-canal ("ITC") hearing aids. Examples of commercially available hearing aids include, but are not limited to, the Phonak™ Ambra™ hearing aid and the Phonak™ Naida™ hearing aid.

The present inventors have determined that conventional ICS systems are susceptible to improvement. For example, the present inventors have determined that some patients would benefit from an ICS system with an external sound processor that is smaller and lighter than those currently available and that this may be accomplished by altering the manner in which power is stored and supplied within the ICS system.

SUMMARY

A headpiece in accordance with one of the present inventions includes a battery, a magnet that is magnetically attracted to the position element of a cochlear stimulator, and a data/power transmission apparatus adapted to receive stimulation data, to transmit the received stimulation data to the cochlear stimulator, and to transmit power from the battery to the cochlear stimulator. The headpiece does not include sound processor circuitry.

A hearing assistance system in accordance with one of the present inventions includes an implantable cochlear stimulator, a hearing assistance device with a battery, sound processor circuitry that converts electrical signals from a microphone into stimulation data, and a data communication apparatus configured to transmit the stimulation data, and a headpiece with a battery and a data/power transmission apparatus adapted to receive the stimulation data, to wirelessly transmit the received stimulation data to the cochlear stimulator receiver apparatus, and to wirelessly transmit power from the battery to the cochlear stimulator receiver apparatus.

A method in accordance with one of the present inventions includes the steps of transmitting stimulation data from an external hearing assistance to a headpiece, wirelessly transmitting the stimulation data from the headpiece to an implanted cochlear stimulator, wirelessly transmitting power stored in a battery of the headpiece to the implanted cochlear stimulator, and electrically stimulating the user's auditory nerve with the implanted cochlear stimulator in response to receipt of the stimulation data from the headpiece.

A hearing assistance system in accordance with one of the present inventions includes an implantable cochlear stimulator, a headpiece with a battery and a magnet that is adapted to receive stimulation data, to wirelessly transmit received stimulation data to the cochlear stimulator, and to wirelessly transmit power from the battery to the cochlear stimulator, a notification source that transmits a notification signal, and a retransmission apparatus that wirelessly receives the notification signal and wirelessly transmits stimulation data to the headpiece in response to receipt of the notification signal.

There are a number of advantages associated with such apparatus, systems and methods. For example, supplying power to an implanted cochlear stimulator with a battery carried by the headpiece facilitates a reduction in the size/weight of the external hearing assistance device (e.g., a BTE sound processor) by an amount that was heretofore attributable to the supply of power to the cochlear stimulator. Moreover, even in those instances where the combined size/weight of the hearing assistance device power supply and the headpiece power supply is the same as that of the power supply of a conventional ICS sound processor, the distribution of the weight makes the present system more comfortable. The present apparatus, systems and methods may also be implemented in electric acoustic stimulation ("EAS") systems where a hearing aid and a cochlear implant are used together in the same ear.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present inventions have application in a wide variety of hearing assistance devices and systems that provide sound (i.e., either sound or a perception of sound) to the hearing impaired as well as others who require such hearing devices on a situational basis. Examples of such hearing assistance devices and systems include hearing aids and ICS systems where an external sound processor communicates with a cochlear implant. The present inventions are not, however, limited to such devices and systems and may be employed in combination with other hearing assistance devices and systems that currently exist, or are yet to be developed.

Figure 1:
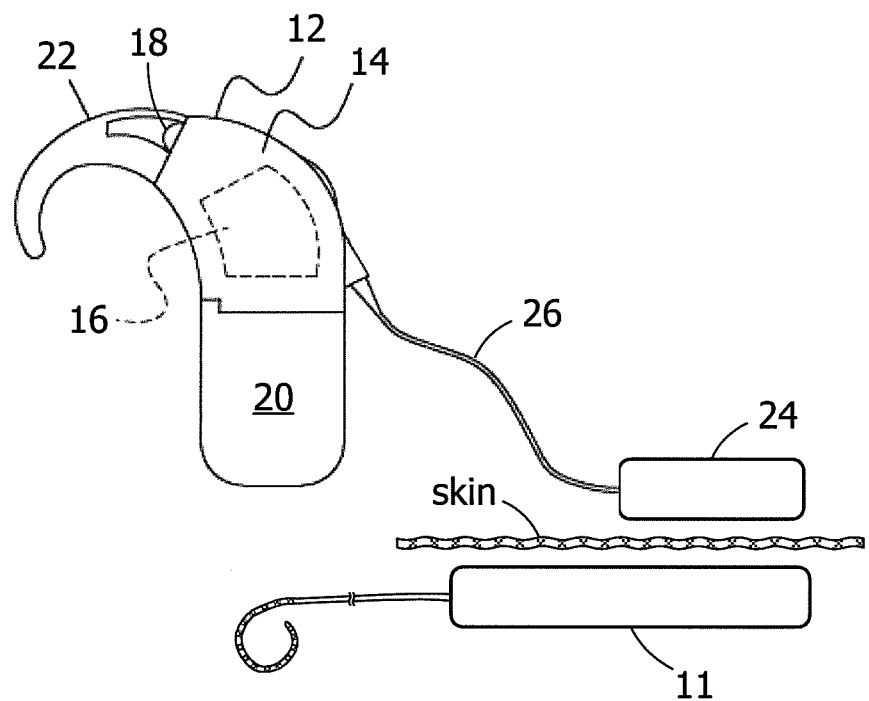
FIG. 1 is a side view of a conventional ICS system with a BTE sound processor, a headpiece and a cochlear implant.
Figure 2:
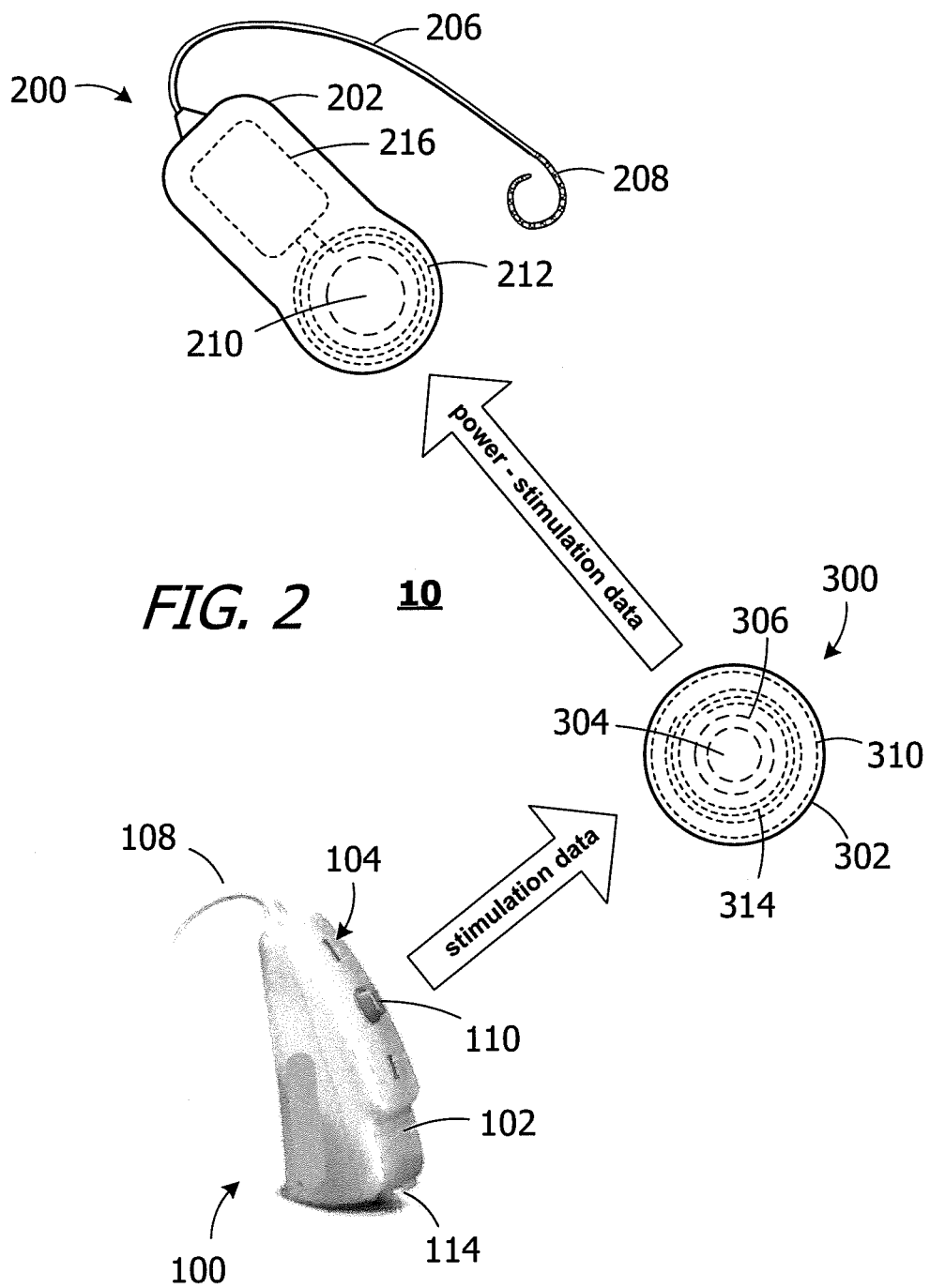
FIG. 2 is a plan view showing components of an ICS system in accordance with one embodiment of a present invention.

One example of a hearing assistance system is the ICS system generally represented by reference numeral 10 in FIG. 2. The exemplary ICS system 10 includes an external BTE hearing assistance device 100, an implantable cochlear simulator 200, and an external head mountable power supply and data receiver/transmitter (or "headpiece") 300. Briefly, the hearing assistance device 100 supplies stimulation data, but not power, to the headpiece 300 by way of a wireless link. The headpiece 300 retransmits the stimulation data to the cochlear simulator 200, and also supplies power from its own battery to the cochlear stimulator, by way of a wireless link.

Figure 3:
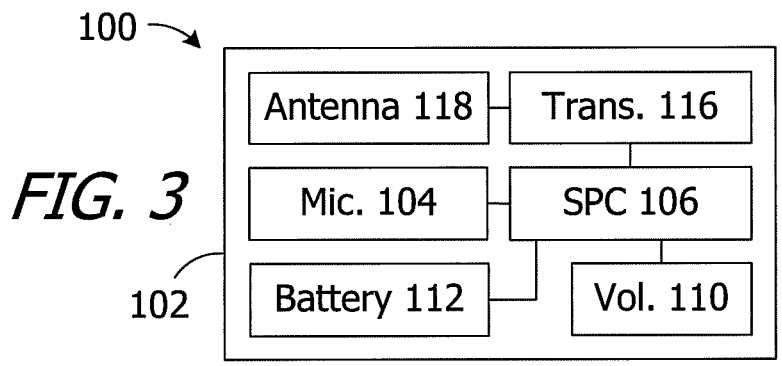
FIG. 3 is a block diagram of a hearing assistance device in accordance with one embodiment of a present invention.

Referring also to FIG. 3, the exemplary BTE hearing assistance device 100 includes a housing 102, a microphone 104, sound processor circuitry ("SPC") 106, and a retention member 108. A speaker (not shown) may be provided in some implementations. A volume control button 110 is positioned on the exterior of the housing 102. The hearing assistance device 100 also includes a primary or secondary battery or other power supply 112 that supplies power to the sound processor circuitry 106 and other power consuming components of the BTE hearing assistance device. In the illustrated implementation, the power supply 112 is carried by a removable battery holder (not shown) that is secured to housing 102 with a latch 114. In other implementations, a secondary battery may be permanently housed within the hearing assistance device and the battery holder may be omitted. Such a hearing assistance device may be placed in a battery charger as necessary.

In the illustrated embodiment, there is also a wireless data link between the BTE hearing assistance device 100 and the headpiece 300. A data transmitter 116 drives a data antenna 118 to transmit stimulation data, but not power, to the headpiece 300. The BTE hearing assistance device 100 does not supply power to the cochlear simulator 200 or headpiece 300. The data transmitter 116 and data antenna 118 are collectively referred to as a data communication apparatus and, in those implementations where the BTE hearing aid wirelessly receives information (e.g., where status information is transmitted from the cochlear simulator 200 to the BTE hearing assistance device 100, either directly or by way of the headpiece 300), the data communication apparatus would include a data transceiver and a data antenna. One example of a suitable data communication apparatus is a near field magnetic induction ("NFMI") apparatus where a data transmitter and coil antenna generate a short range, low-power, non-propagating magnetic field. Other types of wireless links, including but not limited to RF data communication apparatus, may also be employed to transmit stimulation data from the hearing assistance device 100 to the headpiece 300.

Figure 4:
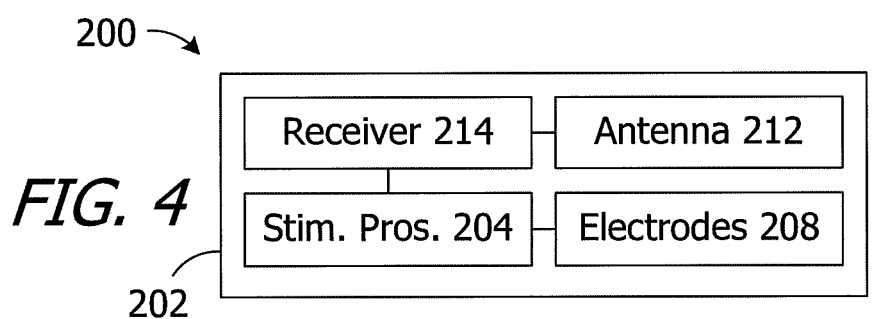
FIG. 4 is a block diagram of an implantable cochlear stimulator in accordance with one embodiment of a present invention.

As illustrated in FIGS. 2 and 4, the exemplary cochlear stimulator 200 includes a flexible housing 202 formed from a silicone elastomer or other suitable material, an internal stimulation processor 204, a cochlear lead 206 with an electrode array 208, and a positioning element (i.e., a magnet or other ferromagnetic material) 210. The cochlear stimulator 200 also includes data and power receiver apparatus which, in the illustrated implementation, consists of an antenna 212 and a receiver 214. The stimulation processor 204 and receiver 214 may be located on a common circuit board 216, or on separate boards. The antenna and receiver 212 and 214 receive stimulation data and power from the headpiece 300. The stimulation data is generated by the hearing assistance device 100 and is retransmitted by the headpiece 300 to the cochlear stimulator 200, while the power that is transmitted by the headpiece to the cochlear stimulator is supplied by the headpiece itself. The antenna 214 may be a coil antenna that is inductively coupled to the coil antenna 314 (discussed below) of the headpiece 300.

As used herein, a "stimulation processor" is a processor that converts the stimulation data from a sound processing device (e.g., the sound processor circuitry 106) into stimulation signals that stimulate the electrodes of an electrode array (e.g., the electrodes in array 208). A "stimulation processor" does not itself convert electrical signals from a microphone into stimulation data and, therefore, is not a "sound processor." It should also be noted that the exemplary implantable cochlear stimulator 200 is not a totally implantable cochlear implant system, nor is it part of such a system. To that end, the cochlear stimulator 200 does not include a microphone, sound processor circuitry, or a battery. The cochlear stimulator 200 relies on another device (here, the BTE hearing assistance device 100) for microphone and sound processing functionality and relies on another device (here, the headpiece 300) for power.

Figure 5:
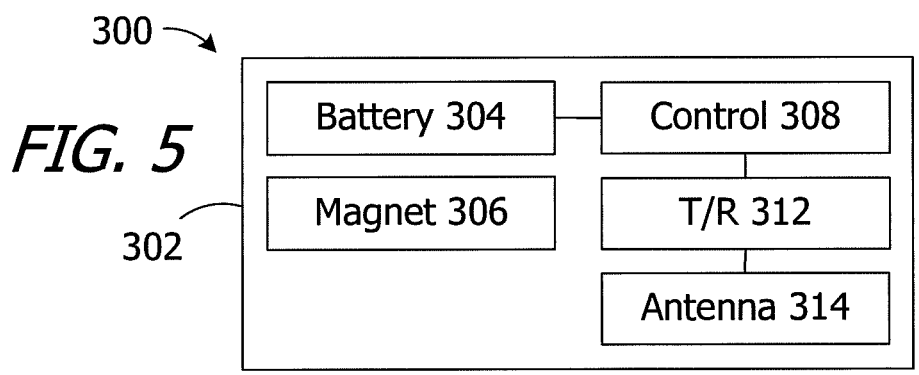
FIG. 5 is a block diagram of a headpiece in accordance with one embodiment of a present invention.

As illustrated in FIGS. 2 and 5, the exemplary external head mountable power supply and data receiver/transmitter (or "headpiece") 300 includes a housing 302, a battery 304 (primary or secondary), a positioning magnet 306 that is attracted to the positioning element 210 of the cochlear stimulator 200, and control circuitry 308 on a circuit board 310. The headpiece 300 also includes apparatus that establishes a wireless link with the cochlear stimulator 200 for retransmission of the stimulation data generated by the hearing assistance device 100, as well as power from the battery 304, to the cochlear stimulator. The data/power transmission apparatus includes a transmitter/receiver (or "transceiver") 312 that drives a coil antenna 314 (or other suitable antenna). The control circuitry 308 controls the flow of power from the battery 304 to the transmitter/receiver 312 and coil antenna 314. The housing 302 includes a battery replacement door (not shown) so that the battery 304 may be removed and replaced as necessary. Alternatively, the secondary battery may be permanently housed within the housing and the door may be omitted. Such a headpiece may be placed in a battery charger as necessary. In the illustrated implementation, there is no on/off switch and the headpiece 300 operates so long as the battery 304 is not fully discharged. An on/off switch may be provided in other implementations. A low power indicator such as an LED may be provided in some implementations. With respect to power transmission level, which is typically a function of the thickness of the skin between the headpiece 300 and the cochlear stimulator 200, the power level may be preset, as it is in the illustrated implementation. In others, a small knob may be provided that allows the power level to be adjusted during the fitting process.

The exemplary headpiece 300 does not include a microphone or sound processor circuitry, and is commensurate in size and shape with a conventional ICS headpiece (e.g., is between about 0.25 inch and 3 inches in diameter in some implementations and between about 0.5 inch and 1.5 inch in other implementations). The headpiece 300 is also not a BTE hearing assistance device. As noted above, the headpiece 300 is a data retransmission device that also provides power to the cochlear stimulator 200.

In at least some implementations, the cochlear stimulator 200 may provide the power supply 300 with information that can be used to, for example, optimize power transmission to the cochlear stimulator by adjusting the transmission level to a level below the maximum level, when possible, to extend the life of the battery 304. For example, information concerning the current supply voltage of the cochlear stimulator 200 may be used by the power supply 300 to modulate power to the cochlear stimulator in real time. The information may be provided in a variety of ways. For example, a low data rate back telemetry link from the cochlear stimulator 200, which is indicative of the tank voltage of the implant (e.g., a single bit which indicates whether the tank voltage is at or below a predetermined level), may be used by the control circuitry 308 to modulate power from the power supply 300. Alternatively, the cochlear stimulator 200 may be configured to alter its effective impedance as a function of the tank voltage. The effective impendence can be detected by the control circuitry 308 and used to modulate power from the power supply 300.

Figure 6:
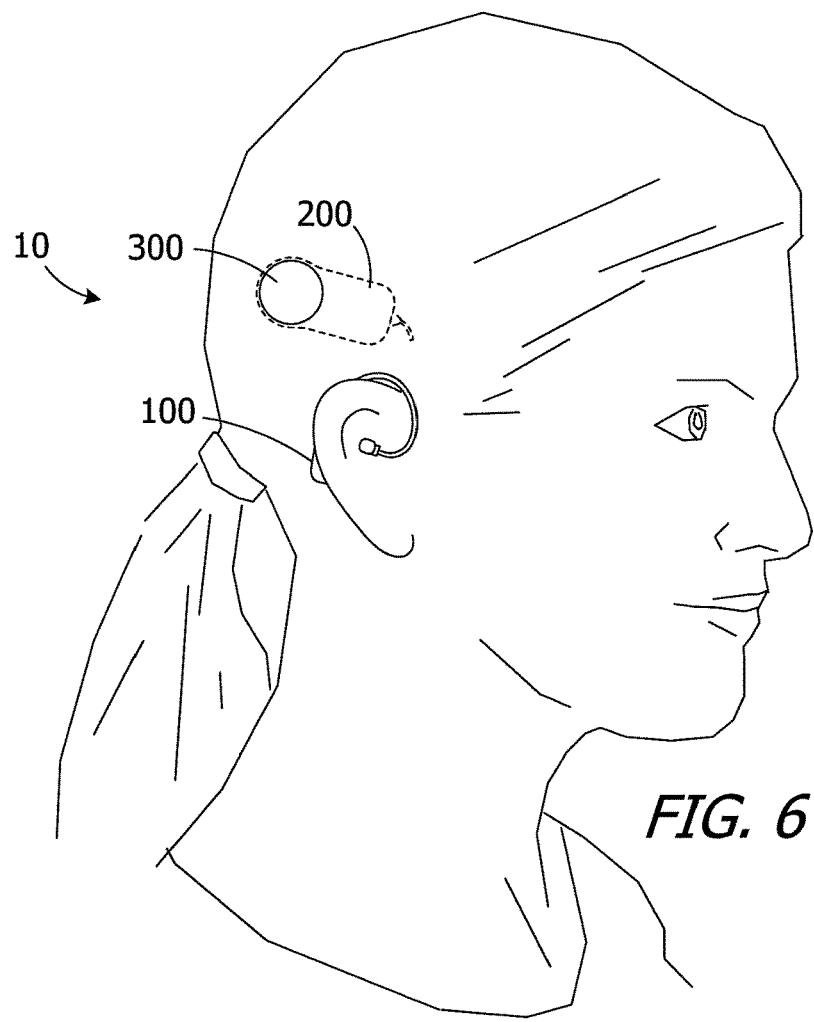
FIG. 6 is a side view showing the ICS system as illustrated in FIGS. 2-5 in use.

During use of the exemplary system 10, and as illustrated in FIG. 6, the BTE hearing assistance device 100 is positioned behind the ear and the headpiece 300 is positioned over the implanted cochlear stimulator 200. The headpiece 300 is not connected to the BTE hearing assistance device 100 by a cable. There is no direct wireless communication between BTE hearing assistance device 100 and the cochlear stimulator 200. The attraction of the power supply magnet 306 to the stimulator magnet or other positioning element 210 aligns the antenna 314 with the cochlear stimulator antenna 212. Power from the power supply battery 304 is supplied to the implanted cochlear stimulator 200. The hearing assistance device microphone 104 picks up ambient sound pressure waves and converts them into electrical signals. The electrical signals are the processed by the sound processor circuitry 106 and converted to stimulation data (e.g., a pulse sequence having varying pulse widths and/or amplitudes). The hearing assistance device data transmitter 116 and antenna 118 establish a wireless link with the headpiece transmitter/receiver 312 and coil antenna 314, so that the hearing assistance device 100 can transmit stimulation data, but not power, to the headpiece 300. The stimulation data is received by the headpiece antenna 314 and transmitter/receiver 312 and is then retransmitted to the implanted cochlear stimulator 200 by way of the wireless link with the antenna and receiver 212 and 214. Power from the headpiece battery 304 is also transmitted to power to the implantable cochlear simulator 200 by way of the wireless link. The stimulation processor 204 converts the data into stimulation signals that stimulate the electrodes in the array 208. The electrode array 208 electrically stimulates the auditory nerve, thereby providing the user with sensory input that is a representation of external sound waves which were sensed by the microphone 104.

Figure 7:
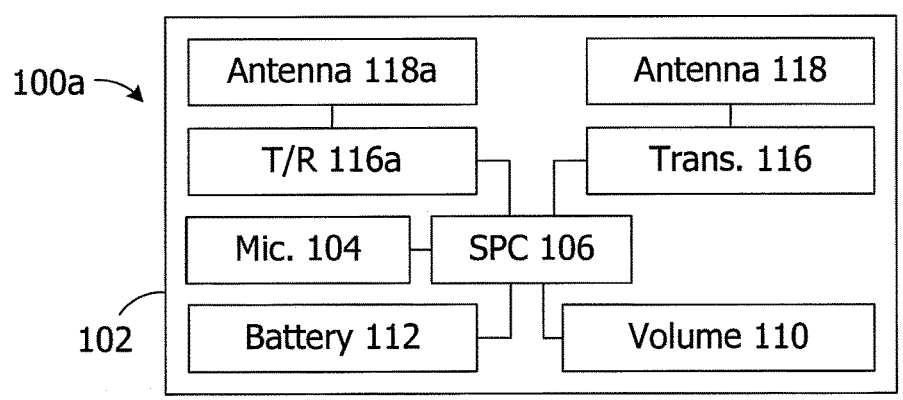
FIG. 7 is a block diagram of a hearing assistance device in accordance with one embodiment of a present invention.

In at least some instances, it may be desirable for the BTE hearing assistance device 100 to wirelessly communicate with devices other than the headpiece 300. Examples of such auxiliary devices include, but are not limited to, remote controls, fitting apparatus, music players, mobile phones and contra-lateral hearing aid. Such communication may be accomplished in a variety of ways. For example, communication by way of the data transmitter 116 and antenna 118 may be time multiplexed. Alternatively, and referring to FIG. 7, the exemplary BTE hearing assistance device 100a is essentially identical to BTE hearing assistance device 100 and similar elements are represented by similar reference numerals. The BTE hearing assistance device 100a may be used in place of the BTE hearing assistance device 100 in the system 10 in the manner described above. Here, however, an auxiliary transmitter/receiver 116a and antenna 118a create a second wireless link with an auxiliary device. For example, the wireless link created with the transmitter 116 and antenna 118 could operate at a first frequency (e.g., 13 MHz) and the transmitter/receiver 116a and antenna 118a could operate at a second frequency (e.g., 10.6 MHz) to create a pair of high bandwidth wireless links. Electrical impulses corresponding to sound are processed by the sound processor 106 for transmission to the headpiece 300 in the manner described above, while control signals from a remote control or fitting apparatus are used to adjust the functionality of the BTE hearing assistance device 100 in conventional fashion.

Figure 8:
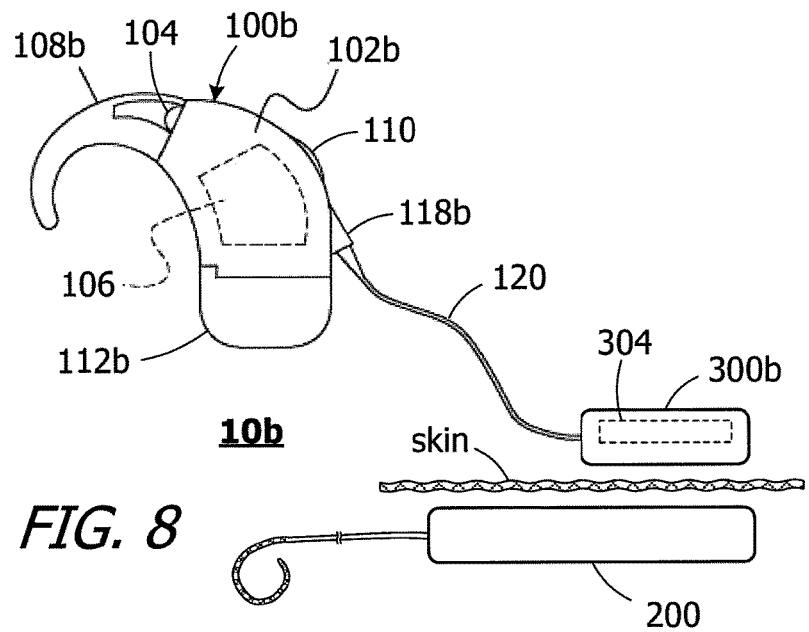
FIG. 8 is a side view of an ICS system in accordance with one embodiment of a present invention.

Another exemplary hearing assistance system is generally represented by reference numeral 10b in FIG. 8. Hearing assistance system 10b is substantially similar to Hearing assistance system 10 and similar elements are represented by similar reference numerals. Here, however, the BTE hearing assistance device 100b transmits stimulation data to the headpiece 300b by way of a wired connection.

Figure 9:
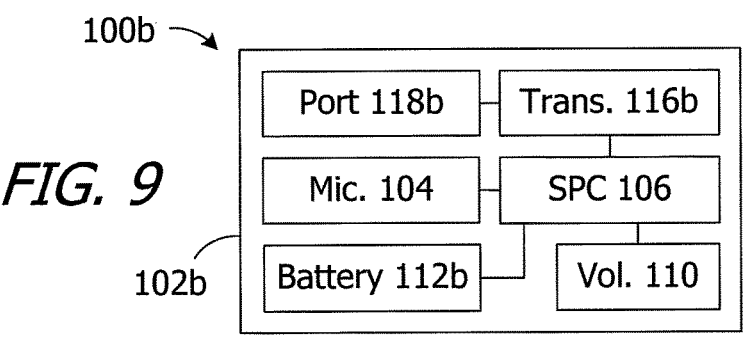
FIG. 9 is a block diagram of a hearing assistance device in accordance with one embodiment of a present invention.

As illustrated in FIGS. 8 and 9, the exemplary hearing assistance device 100b includes a housing 102b, a microphone 104, sound processor circuitry 106, and an ear hook 108b. A speaker (not shown) may be provided in some implementations. A volume control button 110 is positioned on the exterior of the housing 102. The hearing assistance device 100 also includes a battery or other power supply 112b that supplies power to the sound processor circuitry 106 and other power consuming components of the BTE hearing assistance device. There is also a wired data link between the BTE hearing assistance device 100b and the headpiece 300b. In the illustrated embodiment, a wired data transmitter 116b is connected to a data port 118b through which stimulation data, but not power, is transmitted to the headpiece 300b by way of a cable 120 that is connected to the data port. In those instances where the hearing assistance device 100b is an otherwise conventional BTE hearing aid that has been modified so as to embody aspects of the present inventions, the fitting port of the hearing aid may be used as the data port 118b. In those instances where the hearing assistance device 100b is an otherwise conventional BTE cochlear implant sound processor that has been modified so as to embody aspects of the present inventions, the headpiece port may be used as the data port 118b. The data transmitter 116b and data port 118 may be collectively referred to as a data communication apparatus. The BTE hearing assistance device 100b does not supply power to the cochlear simulator 200 or headpiece 300b.

Figure 10:
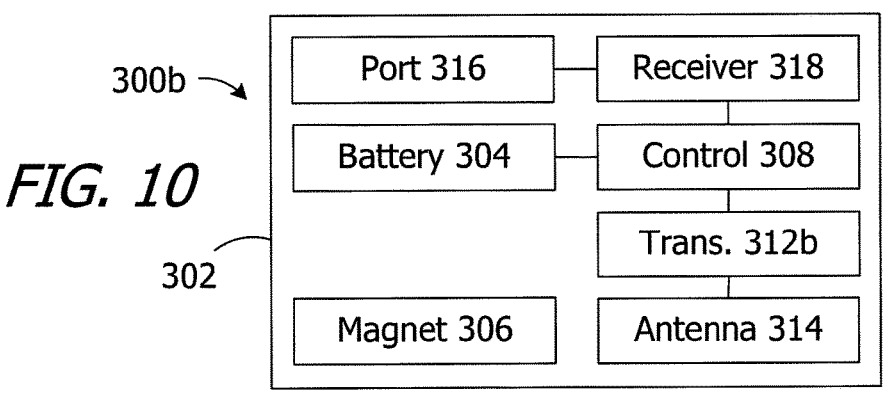
FIG. 10 is a block diagram of a headpiece in accordance with one embodiment of a present invention.

Turning to FIGS. 8 and 10, the exemplary headpiece 300b includes a housing 302, a battery 304 (primary or secondary), a positioning magnet 306 that is attracted to the positioning element 210 of the cochlear stimulator 200, and control circuitry 308 on a circuit board. The headpiece 300a also includes apparatus that establishes a wired link with the hearing assistance device 100a and a wireless link with the cochlear stimulator 200 for retransmission of the stimulation data generated by the hearing assistance device, as well as power from the battery 304, to the cochlear stimulator. Stimulation data is received by way of the data port 316 and data receiver 318. The stimulation data and power are transmitted to the cochlear stimulator with a transmitter 312b that drives a coil antenna 314 (or other suitable antenna).

Figure 11:
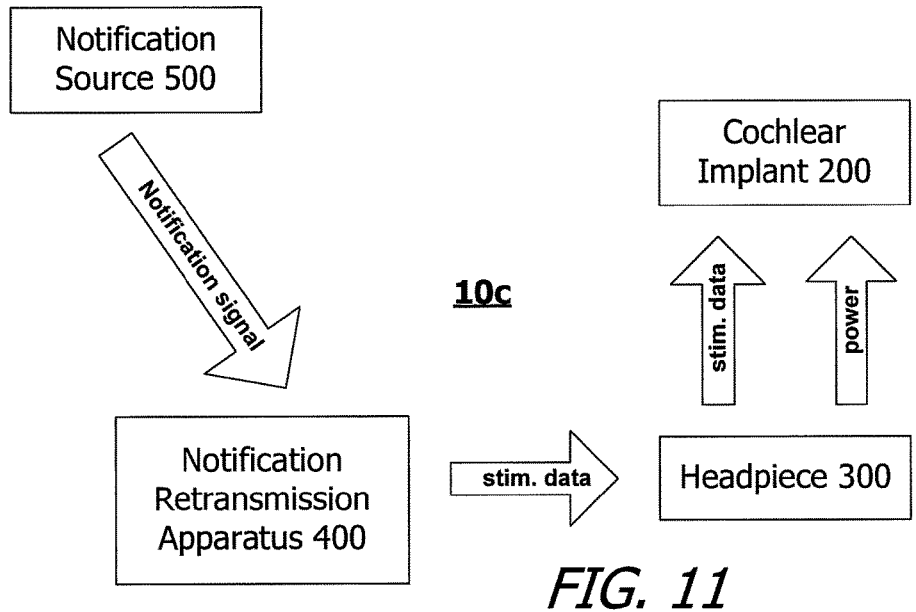
FIG. 11 is a block diagram showing components of an ICS system in accordance with one embodiment of a present invention.

A notification retransmission apparatus may also be used to provide stimulation data indicative of a notification when the BTE hearing assistance device 100 (or other external hearing assistance device) is not in use. For example, although some people may prefer to sleep without their external hearing assistance device, there are many instances where it is important that they receive audible notifications. Such audible notifications include, but are not limited to, an alarm sound (e.g., the sound from a smoke alarm, a $CO_2$ alarm, an alarm clock or home security system), telephone ringing, crying or an alarm notification from a baby monitor, and doorbell ringing. As illustrated for example in FIG. 11, the exemplary system 10c includes the aforementioned cochlear stimulator 200 and headpiece 300 that supplies stimulation data and power to the cochlear stimulator by way of a wireless link. There is no hearing assistance device. Instead, a notification source 500 wirelessly transmits a notification signal to a retransmission apparatus 400 and the retransmission apparatus transmits stimulation data to the cochlear headpiece 300 in response. Exemplary notification sources include, but are not limited to, fire alarms, smoke alarms, $CO_2$ alarms, alarm clocks, telephones, baby monitors and doorbells. BTE and body worn sound processors, hearing aids, and other hearing assistance devices are not "notification sources." The retransmission apparatus 400 may be a bedside device that is sized for placement on a nightstand.

In those instances where the notification signal is an electronic representation of the notification (e.g., an electronic representation of the sound of a smoke alarm), the notification retransmission apparatus 400 converts the notification signal into stimulation data and transmits the stimulation data to the headpiece 300. The headpiece 300 retransmits the stimulation data to the cochlear simulator 200, and also supplies power from its own battery to the cochlear stimulator, by way of a wireless link. In other implementations, the notification signal may simply be a predefined trigger signal or one of a plurality of different trigger signals. Here, the notification retransmission apparatus 400 will transmit predefined stimulation data to the headpiece 300 (e.g., data that corresponds to a predefined sound or series of sounds) in response to the trigger signal. The headpiece 300 supplies power and the simulation data to the cochlear stimulator 200. In still other implementations, the notification signal may be the actual audible notification from the notification source. Here, the notification retransmission apparatus 400 will include a microphone that converts the audible notifications into electrical signals and a controller that determines whether the electrical signals correspond to an alarm or other predetermined notification as opposed to background noise, speech, and other non-notification sounds. If so, the electrical signals are converted into stimulation data by the notification retransmission apparatus 400 and the stimulation data is transmitted to the headpiece 300. The headpiece 300 supplies power and the simulation data to the cochlear stimulator 200. In any case, the resulting stimulation of the cochlea should be sufficient to wake a sleeping person.

Figure 12:
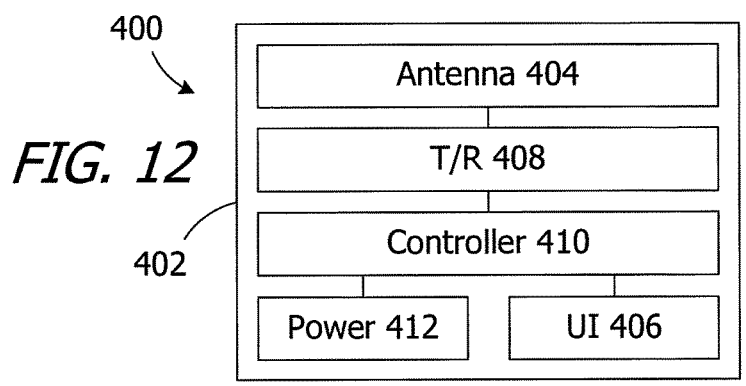
FIG. 12 is block diagram of a retransmission apparatus in accordance with one embodiment of a present invention.
Figure 13:
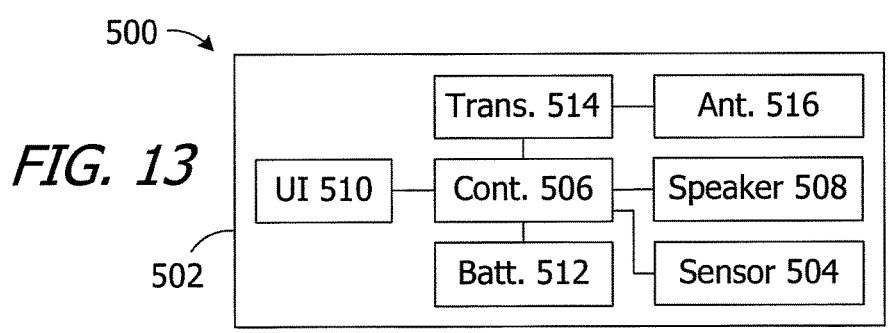
FIG. 13 is a block diagram of a notification source in accordance with one embodiment of a present invention.

Referring to FIG. 12, the exemplary notification retransmission apparatus 400 includes a housing 402, an antenna 404, and a user interface 406. A transmitter/receiver 408, a controller 410, and a power supply 412 are located within the housing 402. The wirelessly transmitted notification signals from the notification source 500 (e.g., a wirelessly transmitted data signal) are received by way of the antenna 404 and transmitter/receiver 408, and are processed by the controller 410. The resulting stimulation data is transmitted by the retransmission apparatus 400 to the headpiece 300 by way of the antenna 404 and transmitter/receiver 408. The transmissions may occur at different frequencies such as, for example, 2.4 GHz Bluetooth transmission from the notification source 500 to the notification retransmission apparatus 400, 10.6 MHz transmission from the retransmission apparatus 400 to the headpiece 300, and 49 MHz transmission from the headpiece 300 to the cochlear simulator 200. In other implementations, a separate antenna and transmitter/receiver may be provided for the notification source to retransmission apparatus wireless link and for the retransmission to cochlear stimulator wireless link.

Turning to FIG. 15, and although the present notification sources are not so limited, the exemplary notification source 500 is in the form of a smoke alarm that includes conventional smoke alarm components such as a housing 502, a smoke sensor 504, a controller 506, a speaker or other sound generator 508, a user interface 510 and a battery 512. The exemplary notification source 500 also includes a transmitter 514 and antenna 516. In response to a signal from the sensor 504, the controller 506 causes sound to be emitted from the speaker 508. The controller 506 also causes the notification signal to be transmitted to the notification retransmission apparatus 400 by way of the transmitter 514 and antenna 516.

It should also be noted that the notification source and the retransmission apparatus may be combined in some instances.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A hearing assistance system, comprising:
an implantable cochlear stimulator, that does not include sound processor circuitry that converts electrical signals from a microphone into stimulation data and does not include a battery, including a position element, receiver apparatus adapted to wirelessly receive power and stimulation data, an electrode array, and a stimulation processor operably connected to the receiver apparatus and to the electrode array;
a hearing assistance device including a battery, sound processor circuitry that converts electrical signals from a microphone into stimulation data, and a data communication apparatus configured to transmit the stimulation data; and
a headpiece, that does not include sound processor circuitry that converts electrical signals from a microphone into stimulation data, including a battery, a magnet that is magnetically attracted to the position element, and a data/power transmission apparatus adapted to receive the stimulation data, to wirelessly transmit the received stimulation data to the cochlear stimulator receiver apparatus, and to wirelessly transmit power from the battery to the cochlear stimulator receiver apparatus;
wherein the hearing assistance device is not connected to the headpiece with a cable during use.

2. A hearing assistance system as claimed in claim 1, wherein the hearing assistance device includes a speaker.

3. A hearing assistance system as claimed in claim 1, wherein
wherein the data/power transmission apparatus comprises a transmitter and a coil antenna.

4. A hearing assistance method, comprising the steps of:
transmitting stimulation data, but not power, from an external hearing assistance device associated with a user's head to a headpiece that is mounted on the exterior of the user's head, that does not include sound processor circuitry that converts electrical signals from a microphone into stimulation data, that includes a housing, a coil antenna within the housing and a battery within the housing, and that is not connected to the external hearing device with a cable, by way of magnetic attraction between the headpiece and a cochlear stimulator implanted within the user's head;
wirelessly transmitting the stimulation data from the headpiece to the implanted cochlear stimulator;
wirelessly transmitting power stored in the battery within headpiece housing to the implanted cochlear stimulator with the coil antenna within the headpiece housing; and
electrically stimulating the user's auditory nerve with the implanted cochlear stimulator in response to receipt of the stimulation data from the headpiece.

5. A hearing assistance method as claimed in claim 4, further comprising the step of:
converting electrical signals from a microphone into the stimulation data with a sound processor located within the external hearing assistance device.

6. A hearing assistance method as claimed in claim 4, further comprising the step of:
powering the implanted cochlear stimulator solely with power wirelessly received from the battery of the headpiece mounted on the exterior of the user's head.

7. A hearing assistance method as claimed in claim 4, wherein the step of transmitting stimulation data comprises wirelessly transmitting stimulation data from the external hearing assistance device to the headpiece.

8. A hearing assistance system, comprising:
an implantable cochlear stimulator including a position element, receiver apparatus adapted to wirelessly receive power and stimulation data, an electrode array, and a stimulation processor operably connected to the receiver apparatus and to the electrode array;
a headpiece including a battery, a magnet that is magnetically attracted to the position element, and a data/power transmission apparatus adapted to receive the stimulation data, to wirelessly transmit received stimulation data to the cochlear stimulator receiver apparatus, and to wirelessly transmit power from the battery to the cochlear stimulator receiver apparatus;
a notification source that transmits a notification signal; and
a retransmission apparatus, including a data communication apparatus, that is not part of or attached to an external hearing device and that wirelessly receives the notification signal and wirelessly transmits stimulation data to the headpiece in response to receipt of the notification signal.

9. A hearing assistance system as claimed in claim 8, wherein the notification signal comprises one or more of an electronic representation of a notification sound, a trigger signal, and an audible notification.

10. A hearing assistance system as claimed in claim 8, wherein the headpiece does not include sound processor circuitry.

\* \* \* \* \*